US00PP31964P2

(12) United States Plant Patent
Wood

(10) Patent No.: US PP31,964 P2
(45) Date of Patent: Jul. 14, 2020

(54) ***COTINUS* PLANT NAMED 'SMCCDLP'**

(50) Latin Name: *Cotinus coggygria*
Varietal Denomination: SMCCDLP

(71) Applicant: Timothy D Wood, Spring Lake, MI (US)

(72) Inventor: Timothy D Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 0 days.

(21) Appl. No.: 16/501,064

(22) Filed: Feb. 14, 2019

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Cassandra Bright

(57) ABSTRACT

A new and distinct *Cotinus* cultivar named 'SMCCDLP' is disclosed, characterized by large maroon flower plumes. Plants are moderately vigorous, densely branching, upright and rounded in form. The new variety is a *Cotinus*, normally produced as an outdoor garden or container plant.

2 Drawing Sheets

Latin name of the genus and species: *Cotinus coggygria*. Variety denomination: 'SMCCDLP'.

BACKGROUND OF THE INVENTION

The new *Cotinus* cultivar is a product of a planned breeding program conducted by the inventor in Grand Haven, Mich. The objective of the breeding program was to produce *Cotinus coggygria* varieties with new foliage colors. The open pollination resulting in this new variety was made during the Summer of 2011.

The seed parent is the unpatented *Cotinus coggygria* 'Little Ruby'. The pollen parent is unknown. The new variety was identified as a potentially interesting selection during the Summer of 2013 in Grand Haven, Mich.

Asexual reproduction of the new cultivar 'SMCCDLP' was first performed in the Summer of 2013 at a commercial nursery in Grand Haven, Mich., using vegetative softwood cuttings. Subsequent propagation has shown that the unique features of this cultivar are stable and reproduced true to type in successive generations.

SUMMARY OF THE INVENTION

The cultivar 'SMCCDLP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMCCDLP' These characteristics in combination distinguish 'SMCCDLP' as a new and distinct *Cotinus* cultivar:

1. Large maroon flower plumes.
2. Exceptionally large quantity of branches, forming a dense shrubby plant.

PARENT COMPARISON

Plants of the new cultivar 'SMCCDLP' are similar to plants of the seed parent variety in most horticultural characteristics, however, plants of the new cultivar 'SMCCDLP' differ in the following;

1. Grown under identical conditions, the new variety grows approximately 20 to 30% percent wider and about 30% taller than the parent.

COMMERCIAL COMPARISON

Plants of the new cultivar 'SMCCDLP' can be compared to the variety *Cotinus* 'Royal Purple', unpatented. These varieties are similar in most horticultural characteristics however, 'SMCCDLP' differs in the following:

1. The new variety has smaller, narrower elliptic leaves; comparator has larger, rounder leaves.
2. New cultivar is more shrub-like, while the comparator is more tree-like.
3. New variety's foliage is more purple; comparator's foliage is more red.

BRIEF DESCRIPTION OF THE PHOTOGRAPHS

Figure 1:
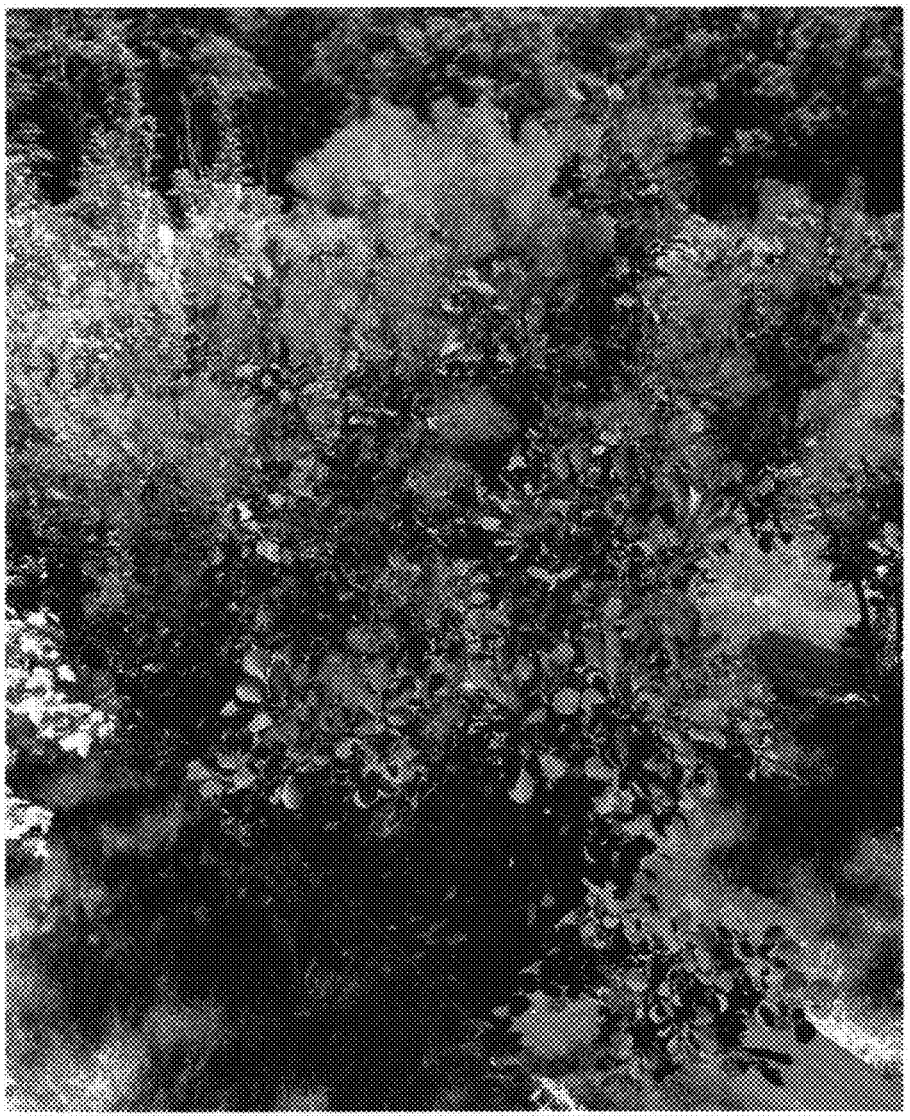

The accompanying photograph in FIG. 1 illustrates in full color a typical mature plant of 'SMCCDLP' grown outdoors, at approximately 5 years old, during Spring.

Figure 2:
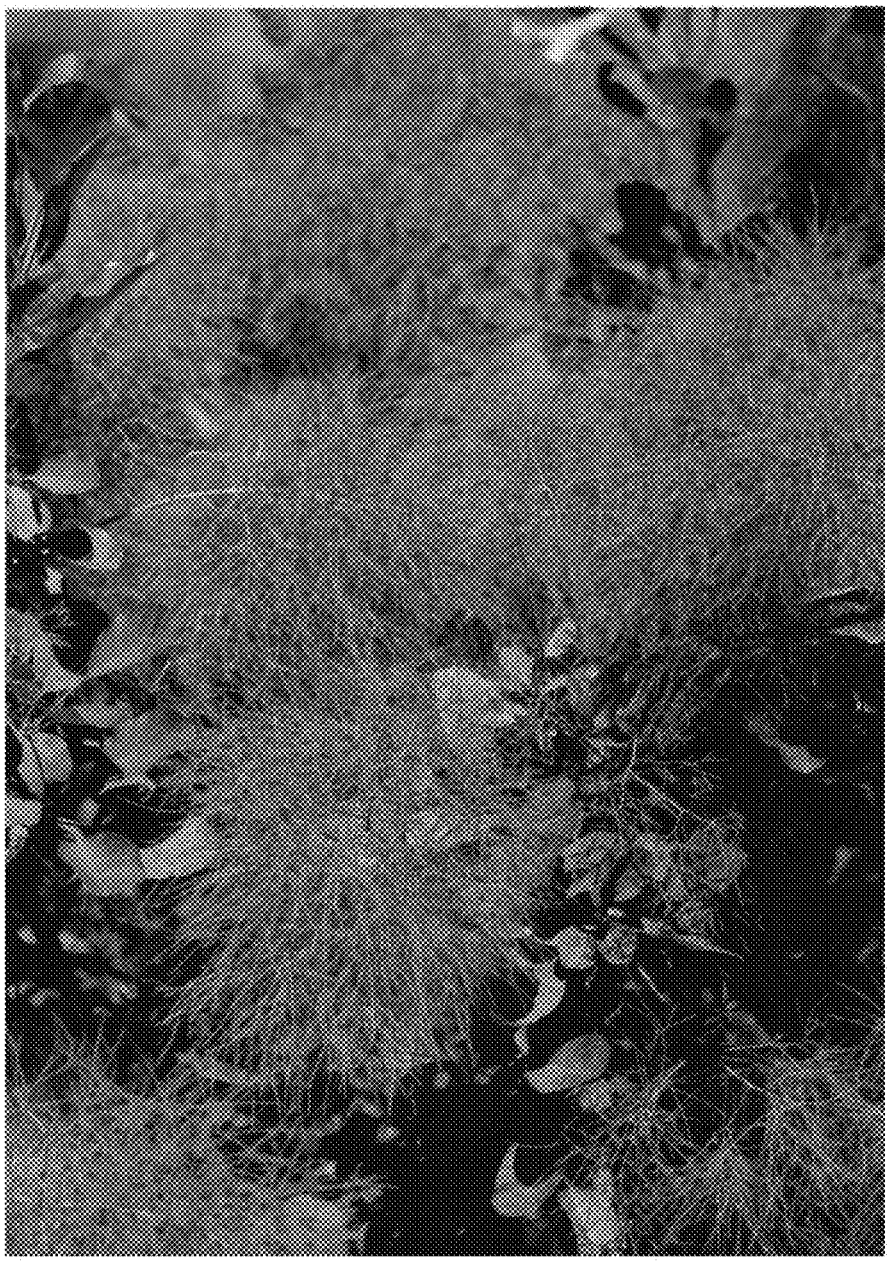

FIG. 2 illustrates a closeup view of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6$^{th}$ edition, except where general terms of ordinary dictionary significance are used. The following observations and measurements describe 'SMCCDLP' plants grown in a polyhouse in Grand Haven, Mich. Measurements were taken during May and August. The plants were about 1-2 years old in 5 gallon containers. The growing temperature ranged from approximately 18° C. to 27° C. during the day and 5°

C. to 10° C. at night. Measurements and numerical values represent averages of typical plant types.

Botanical classification: *Cotinus coggygria* 'SMCCDLP'.

PROPAGATION

Time to initiate roots: 6 weeks at approximately 25° C.

Time to produce a rooted young plant: 12 weeks.

Root description: Fibrous, medium thickness, dense, freely branched. White in color, not effectively measured with a color chart.

PLANT

Plant type: Perennial shrub.

Age of plant described: 1 to 2 years old.

Growth habit: Upright.

Pot size of plant described: 5 gallon pot.

Overall plant shape: Upright and slightly rounded.

Height: 39 cm.

Plant spread: 37 cm.

Plant vigor: Moderate.

Branching characteristics: No basal branching. Pinching not required.

Length of primary lateral branches: 18 cm.

Diameter of lateral branches: 4 mm.

Quantity of lateral branches: 12.

Stem:

- *Shape*.—Round.
- *Strength*.—Flexible.
- *Color*.—RHS Greyed-Orange 177B.
- *Angle of attachment*.—Upright, 0-45°.
- *Texture*.—Glabrous.

Internode length: 1 cm.

FOLIAGE

Leaf:

- *Arrangement*.—Alternate, single.
- *Leaf shape*.—Orbicular to elliptic.
- *Length*.—4.5 cm.
- *Width*.—3.75 cm.
- *Apex*.—Obtuse.
- *Base*.—Attenuate.
- *Margin*.—Slightly crenate.
- *Texture of top surface*.—Smooth.
- *Texture of bottom surface*.—Smooth, with noticeable veins.
- *Color*.—Young foliage upper side: RHS Grey-Purple N187A. Young foliage under side: RHS Grey-Brown N200B. Mature foliage upper side: RHS Green NN137A, during late Summer. Mature foliage under side: RHS Green NN137D, during late Summer. Fall foliage: No significant change observed.
- *Venation*.—Pattern: Pinnate. Color upper side: RHS Greyed-Purple 185B to Green 143C. Color under side: RHS Yellow-Green 143C.
- *Petiole*.—Average Length: 4.75 cm. Diameter: 1 mm. Petiole color upper side: RHS Yellow-green 144A. Petiole color lower side: RHS Yellow-green 144A. Petiole Texture upper side: Smooth. Petiole Texture lower side: Smooth.

FLOWER

Flowering season: Spring, around May in Grand Haven, Mich.

Inflorescence:

- *Type*.—Terminal panicle.
- *Length/height*.—Average 15.8 cm.
- *Width*.—Average 14 cm.
- *Flowers per panicle*.—Potential range of approximately 500 to 2000.

Flower:

- *Diameter*.—5 mm.
- *Height*.—2 mm.
- *Persistent or self-cleaning*.—Self-cleaning.
- *Fragrance*.—None detected.

Flower bud:

- *Diameter*.—About 1 mm.
- *Height*.—About 0.5 mm.
- *Color*.—Near RHS Yellow-Green 150B.

Petal:

- *Number*.—5.
- *Fused*.—Not fused.
- *Shape*.—Ovate.
- *Margin*.—Entire.
- *Apex*.—Acute.
- *Base*.—Cuneate.
- *Length*.—2 mm.
- *Width*.—15 mm.
- *Color*.—Fully opened, upper side: RHS Yellow-Green 150C. Fully opened, under side: RHS Yellow-Green 150C.
- *Petaloids*.—Absent.

Sepal:

- *Number*.—4-5.
- *Arrangement*.—Rotate.
- *Shape*.—Ovate.
- *Length*.—1 mm.
- *Width*.—1 mm.
- *Texture, upper and under side*.—Glabrous.
- *Color*.—RHS Yellow-Green 144C.

Calyx:

- *Shape*.—Campanulate.
- *Length*.—1 mm.
- *Diameter*.—3 mm.

Peduncle:

- *Length*.—15.8 cm.
- *Diameter*.—2 mm.
- *Strength*.—Moderate.
- *Texture*.—Glabrous.
- *Color*.—RHS Greyed-Purple 187A.

Pedicel:

- *Length*.—Flowered — 6 mm; Flowerless — 8 mm.
- *Texture*.—Pubescent (more pubescence on flowerless).
- *Color*.—RHS Greyed-Purple 187A.

REPRODUCTIVE ORGANS

Stamens:

- *Number*.—5.
- *Filament*.—Length: 1 mm. Color: RHS Yellow-Green 144B.

Anthers:

*Shape*.—Kidney-shaped.

*Color*.—RHS Yellow-Orange 15A.

*Pollen*.—Scant.

*Pollen color*.—RHS Yellow-Orange 15A.

Pistil:

*Number*.—1.

*Length*.—Less than 1 mm.

*Style*.—Length: Less than 1 mm. Color: RHS Yellow-Green 144B.

*Stigma*.—Shape: Club-shaped. Color: RHS Yellow-Green 144B. Ovary Color: RHS Yellow-Green 144B.

OTHER CHARACTERISTICS

Seeds and fruits: Not observed to date.

Disease/pest resistance: Neither resistance nor susceptibility to normal diseases and pests of *Cotinus coggygria* have been observed.

Garden performance: Good tolerance, performs well in humid conditions.

Temperature tolerance: Typical range USDA zones 4 through 9.

What is claimed is:

1. A new and distinct cultivar of *Cotinus* plant named 'SMCCDLP' as herein illustrated and described.

* * * * *